United States Patent
Douglas et al.

(10) Patent No.: US 10,668,249 B2
(45) Date of Patent: *Jun. 2, 2020

(54) CLEAN INTERMITTENT CATHETER HAVING EXTERNAL FLOW PATHS

(71) Applicant: Progeny Concepts, LLC, Newtown Square, PA (US)

(72) Inventors: Peter F. Douglas, Newtown Square, PA (US); Emily Ho, Wayne, PA (US)

(73) Assignee: Progeny Concepts, LLC, Newtown Square, PA (US)

( * ) Notice: Subject to any disclaimer, the term of this patent is extended or adjusted under 35 U.S.C. 154(b) by 254 days.

This patent is subject to a terminal disclaimer.

(21) Appl. No.: 15/646,603

(22) Filed: Jul. 11, 2017

(65) Prior Publication Data

US 2017/0304588 A1    Oct. 26, 2017

Related U.S. Application Data

(63) Continuation of application No. 14/212,258, filed on Mar. 14, 2014, now Pat. No. 9,731,095.

(51) Int. Cl.
*A61M 25/00* (2006.01)
*A61M 25/01* (2006.01)

(52) U.S. Cl.
CPC ...... *A61M 25/007* (2013.01); *A61M 25/0071* (2013.01); *A61M 25/0111* (2013.01); *A61M 2210/1089* (2013.01)

(58) Field of Classification Search
CPC .......................... A61M 3/0279; A61M 3/0287
See application file for complete search history.

(56) References Cited

U.S. PATENT DOCUMENTS

| | | | | |
|---|---|---|---|---|
| 3,630,206 A | * | 12/1971 | Gingold | A61M 25/0017 604/103.08 |
| 3,815,608 A | * | 6/1974 | Spinosa | A61M 25/0017 604/105 |
| 4,846,791 A | | 7/1989 | Hattler et al. | |
| 4,867,747 A | | 9/1989 | Yarger | |
| 5,738,654 A | * | 4/1998 | Tihon | A61F 2/04 604/105 |
| 6,080,142 A | * | 6/2000 | Sachse | A61F 2/0027 604/102.01 |
| 6,221,060 B1 | * | 4/2001 | Willard | A61M 25/0075 600/29 |
| 7,608,085 B2 | * | 10/2009 | Barrientos | A61B 17/0482 606/144 |
| 2004/0006311 A1 | * | 1/2004 | Shchervinsky | A61M 1/008 604/164.01 |
| 2006/0116661 A1 | * | 6/2006 | Tanghoej | A61M 25/0017 604/540 |
| 2009/0005645 A1 | * | 1/2009 | Frassica | A61B 1/0008 600/137 |
| 2011/0196487 A1 | | 8/2011 | Badawi et al. | |

(Continued)

*Primary Examiner* — Adam Marcetich
(74) *Attorney, Agent, or Firm* — Barley Snyder

(57) ABSTRACT

A catheter is provided with a distal portion, a proximal portion, and a plurality of drainage eyes disposed at a junction between the distal portion and the proximal portion. The distal portion includes a tip, a plurality of elongated ribs, and a plurality of external flow paths. The proximal portion includes an internal lumen and a proximal end. The plurality of drainage eyes communicate with the plurality of external flow paths and the internal lumen.

15 Claims, 16 Drawing Sheets

(56) References Cited

U.S. PATENT DOCUMENTS

| | | | |
|---|---|---|---|
| 2011/0213453 A1 | 9/2011 | Mangiardi | |
| 2012/0165791 A1* | 6/2012 | Lovmar | A61M 25/0017 604/544 |
| 2012/0239004 A1* | 9/2012 | Wong | A61M 25/0017 604/540 |
| 2014/0378951 A1* | 12/2014 | Dye | A61M 25/0017 604/544 |
| 2015/0018802 A1* | 1/2015 | Zvuloni | A61M 25/0075 604/517 |

* cited by examiner

CLEAN INTERMITTENT CATHETER HAVING EXTERNAL FLOW PATHS

CROSS REFERENCE TO RELATED APPLICATION

This application is a continuation application of U.S. patent application Ser. No. 14/212,258, filed Mar. 14, 2014.

FIELD OF THE INVENTION

This invention generally relates a catheter and, in particular, an intermittent catheter.

BACKGROUND

Current Clean Intermittent Catheters ("CIC") are single use catheters used for bladder drainage by patients who cannot control either their urinary sphincter muscle or bladder muscles. Conventional CICs are tubular structures having a cylindrical wall with single or multiple openings or drainage eyes in its distal end that communicates with an interior drainage lumen. In use, conventional CICs are inserted into the urethra, through the urinary sphincter (holding it open) and into the bladder for drainage. Once in the bladder, any urine present will drain through the drainage eye, into the internal lumen and through the catheter, into a urine bag or other structure that is connected to the proximal end of the CIC.

One problem seen today with conventional catheters is there is a high Urinary Tract Infection ("UTI") rate among users who self-catheterize due to bacteria being pushed up from the urethra towards and into the bladder as the catheter is inserted. In normal bladder voiding without a catheter, urine flushes the urethra and any existing bacteria away from the bladder as its flows reducing the chance of UTI, however, because with current CICs, the urine flows through the lumen on the interior of the catheter, flushing of the urethra does not occur.

Another problem experienced with current CICs is that it is very difficult to obtain complete voiding of the bladder. Minimizing residual urine in the bladder depends on accurate positioning of the CIC in the bladder, which is oftentimes difficult to ensure. In particular, the drainage eye of conventional CICs must be accurately positioned with respect to the internal neck of the bladder in order to be relatively certain of removing the maximum amount of urine. Additionally, the soft tissue in the neck area of the bladder sometimes has a tendency to get sucked into the drainage eye, making it difficult to completely drain the bladder.

SUMMARY

Embodiments of the present invention disclosed herein address the above-described problems associated with current CICs.

BRIEF DESCRIPTION OF THE DRAWINGS

Various other objects, features and many of the attendant advantages of the invention will be readily appreciated as the same becomes better understood by reference to the following detailed description of the preferred embodiment when considered in connection with the accompanying drawings, in which.

DETAILED DESCRIPTION OF THE EMBODIMENT(S)

Figure 1A:
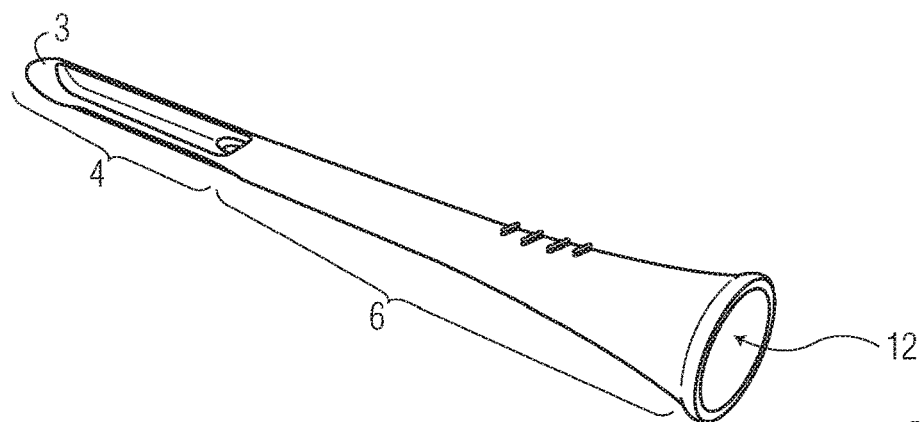
FIG. 1A shows a rear perspective view of a CIC according to the invention.
Figure 1B:
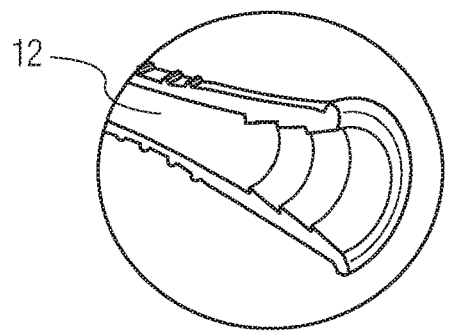
FIG. 1B shows a close up of an internal lumen disposed at one end of the CIC of FIG. 1.
Figure 1C:
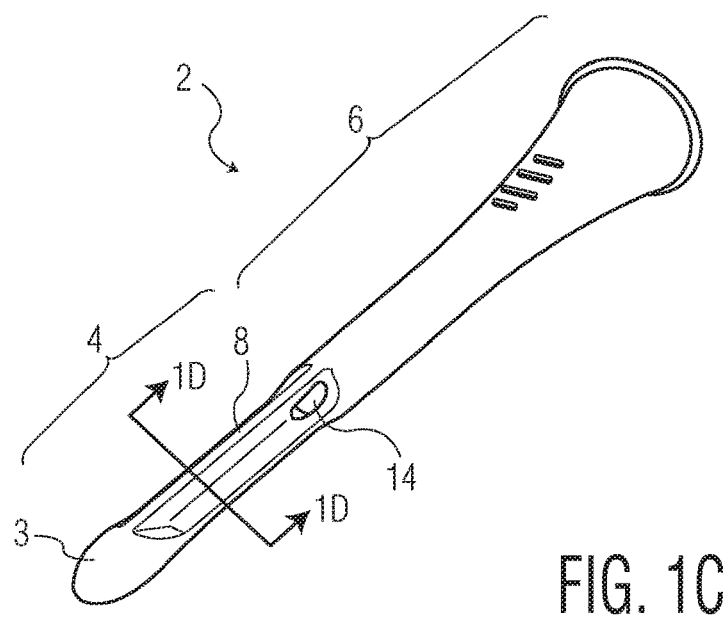
FIG. 1C shows a front perspective view of the CIC of FIG. 1A.
Figure 1D:
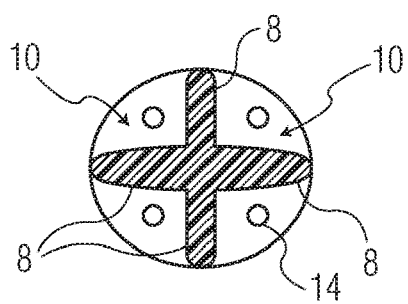
FIG. 1D shows a section of the CIC of FIG. 1 taken along line 1D-1D.
Figure 2A:
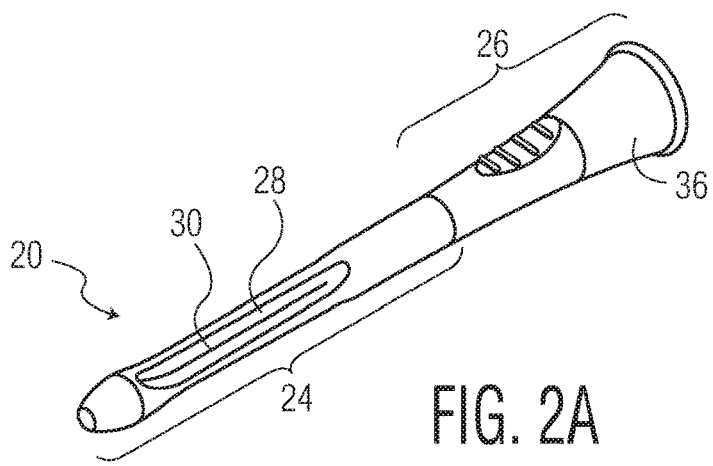
FIG. 2A shows a front perspective view of another CIC, according to the invention.
Figure 2B:
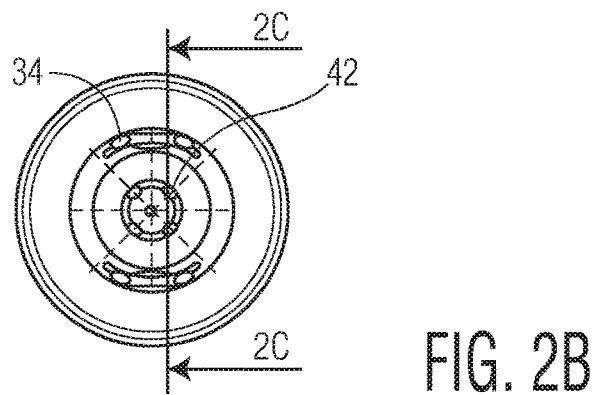
FIG. 2B shows a front view of the CIC of FIG. 2A.
Figure 2C:
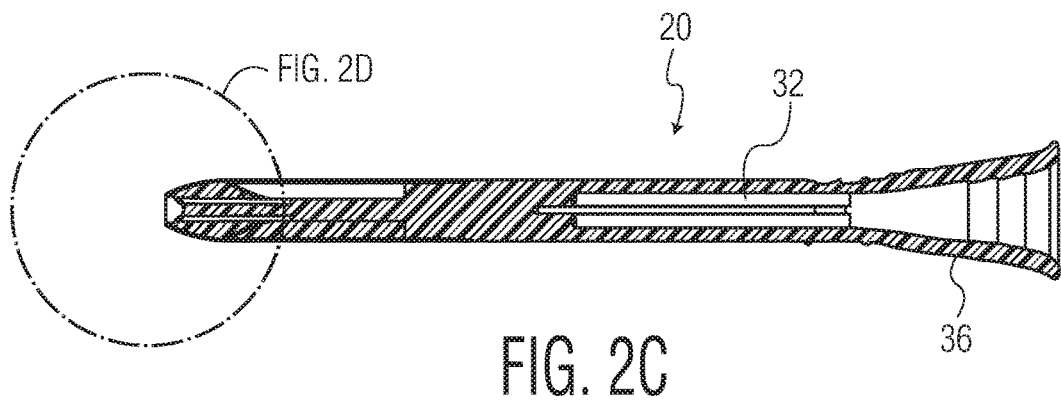
FIG. 2C shows a sectional view of the CIC of FIG. 2B taken along 2B-2B.
Figure 2D:
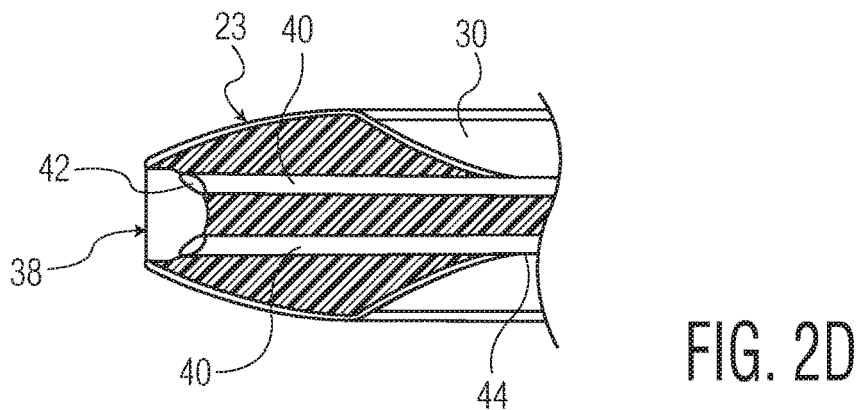
FIG. 2D shows a close up sectional view of a tip of the CIC of FIG. 2B, taken along line.
Figure 3A:
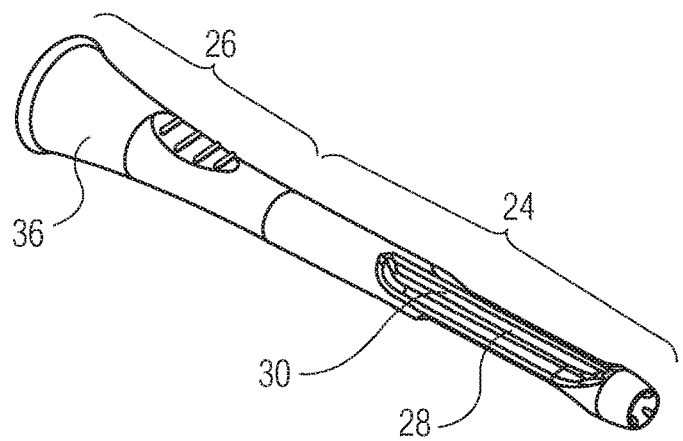
FIG. 3A shows front left perspective view of another CIC according to the invention.
Figure 3B:
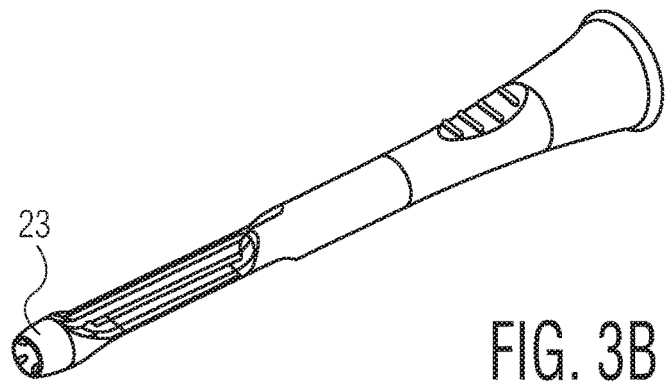
FIG. 3B shows front right perspective view of the CIC of FIG. 3A.
Figure 3C:
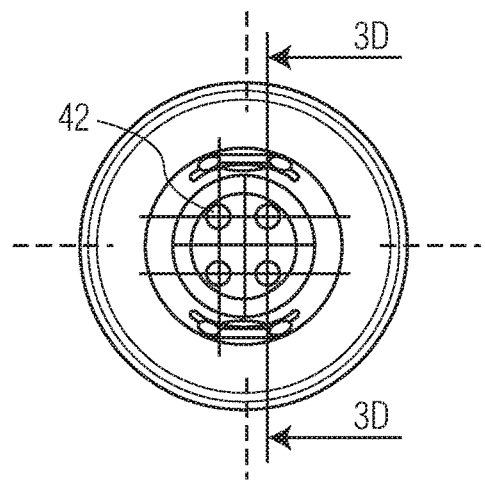
FIG. 3C shows front view of the CIC of FIGS. 3A and 3B.
Figure 3D:
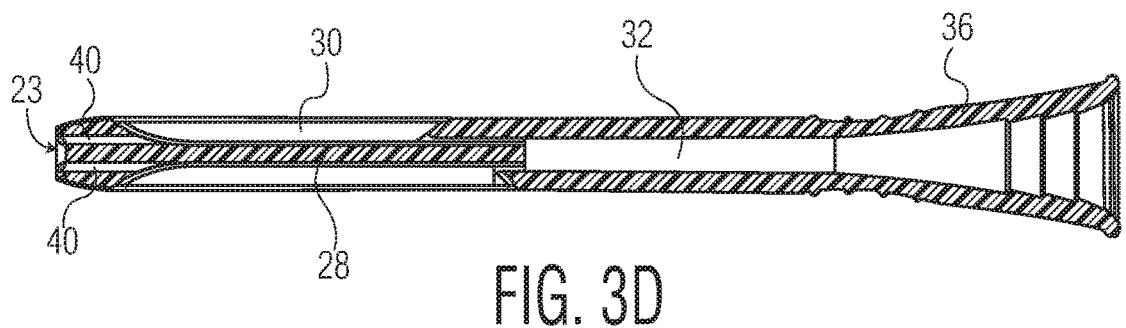
FIG. 3D shows a sectional view of the CIC of FIG. 3C taken along line 3C-3C.
Figure 4A:
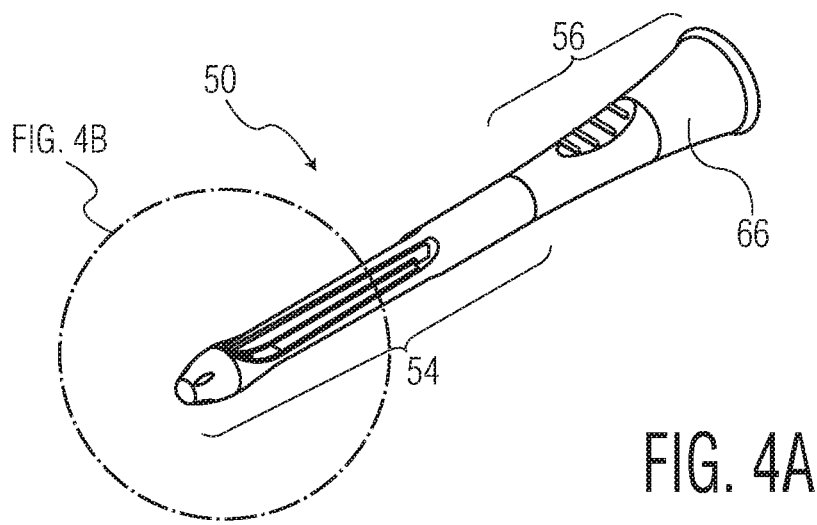
FIG. 4A shows a front perspective view of another CIC according to the invention.
Figure 4B:
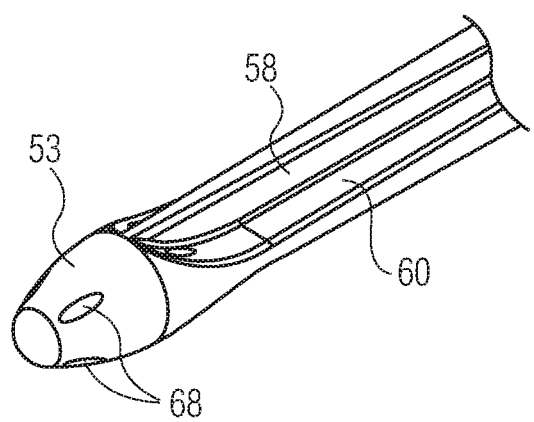
FIG. 4B shows a close up view of a trip of the another CIC of FIG. 4A.
Figure 4C:
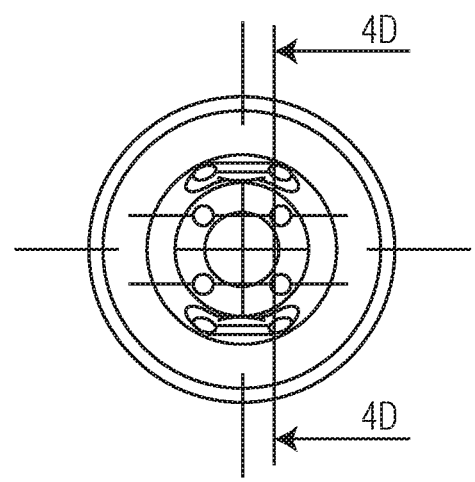
FIG. 4C shows a front view of the CIC of FIG. 4A.
Figure 4D:
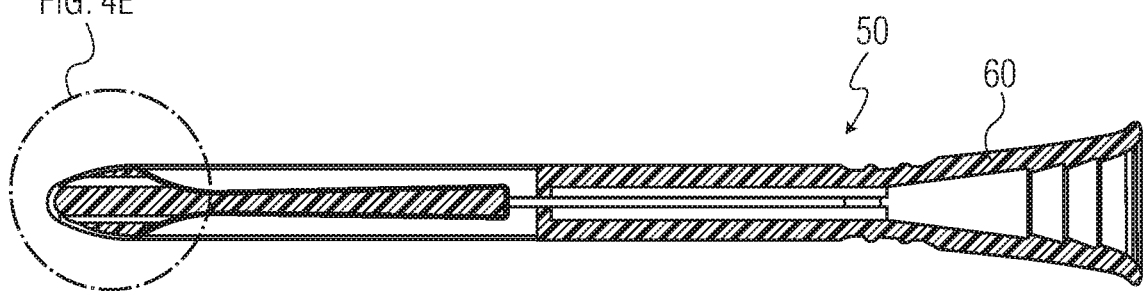
FIG. 4D shows a sectional view of the CIC of FIG. 4C taken along line 4C-4C.
Figure 4E:
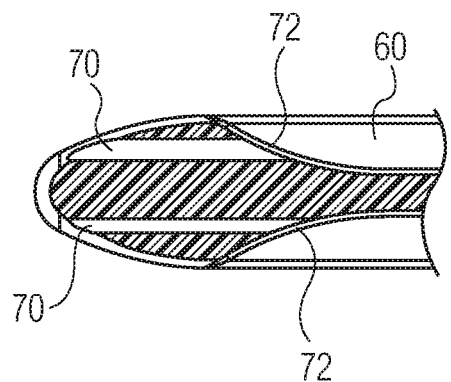
FIG. 4E shows a close up view of the view.
Figure 5A:
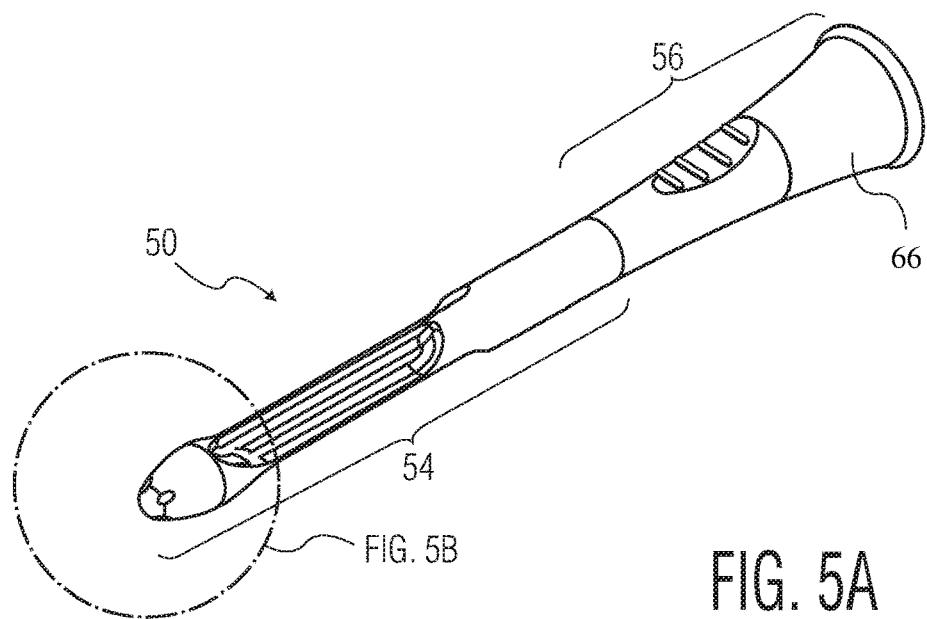
FIG. 5A shows a front perspective view of another CIC according to the invention.
Figure 5B:
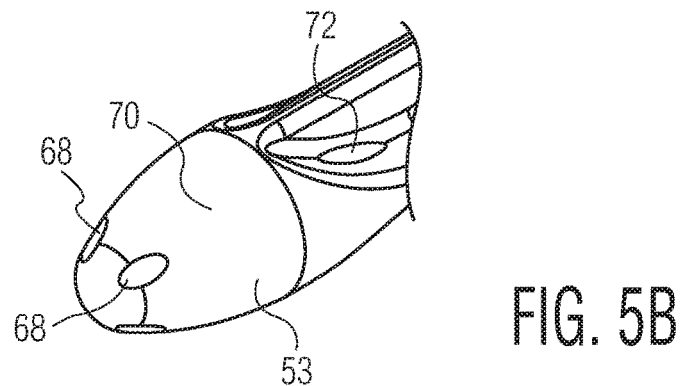
FIG. 5B shows a close up view of a tip of the CIC of FIG. 5A.
Figure 5C:
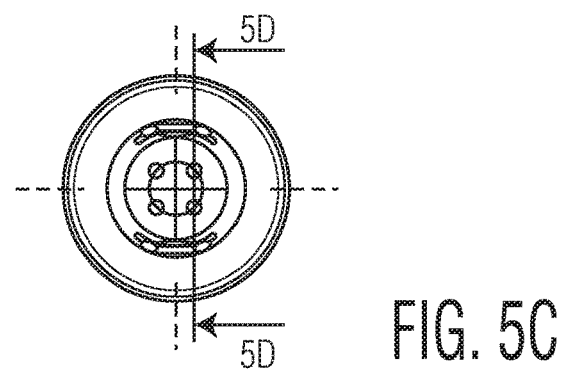
FIG. 5C shows a front view of the CIC of FIG. 5A.
Figure 5D:
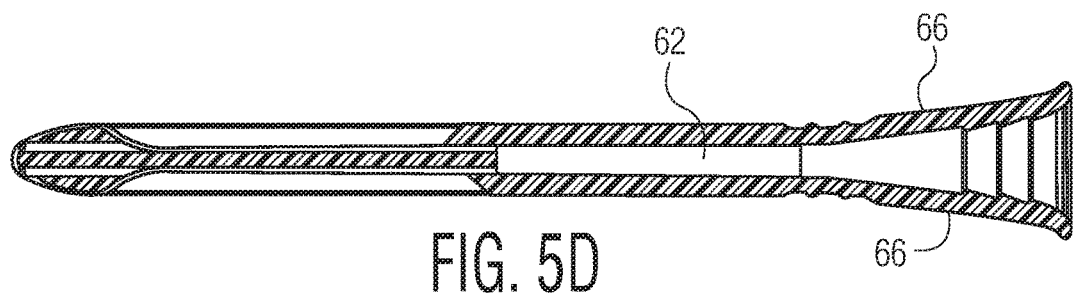
FIG. 5D shows a sectional view of the CIC of FIG. 5C taken along line 5C-5C.
Figure 6A:
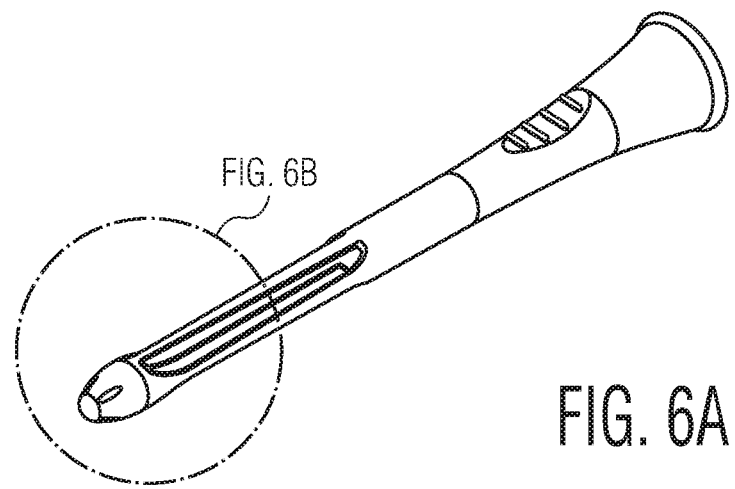
FIG. 6A shows a front perspective view of another CIC according to the invention.
Figure 6B:
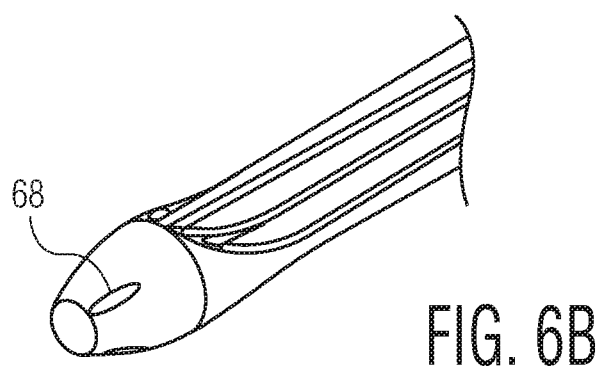
FIG. 6B shows a close up view of a trip of the another CIC of FIG. 6A.
Figure 6C:
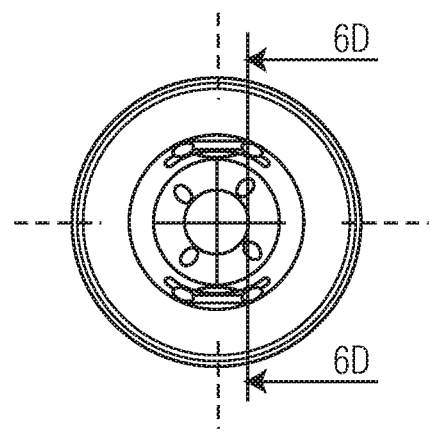
FIG. 6C shows a front view of the CIC of FIG. 6A.
Figure 6D:
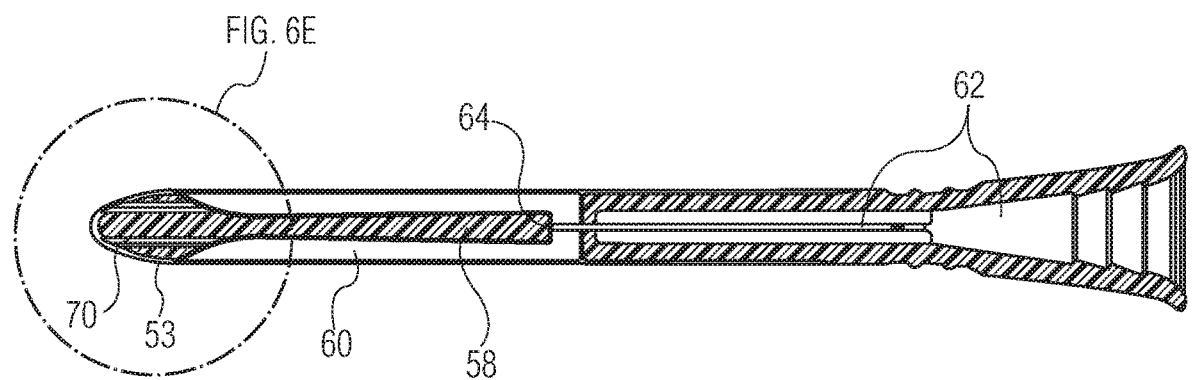
FIG. 6D shows a sectional view of the CIC of FIG. 4C taken along line 6C-6C.
Figure 6E:
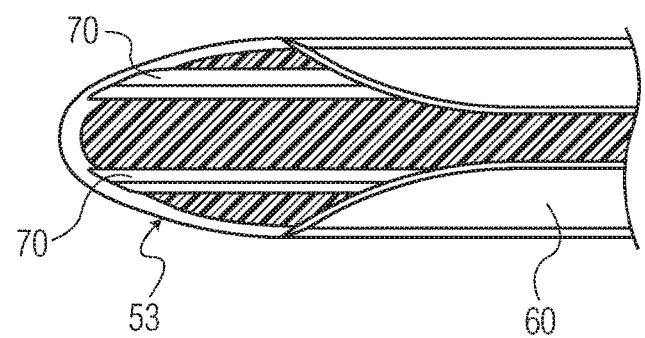
FIG. 6E shows a close up view of the view.
Figure 7:
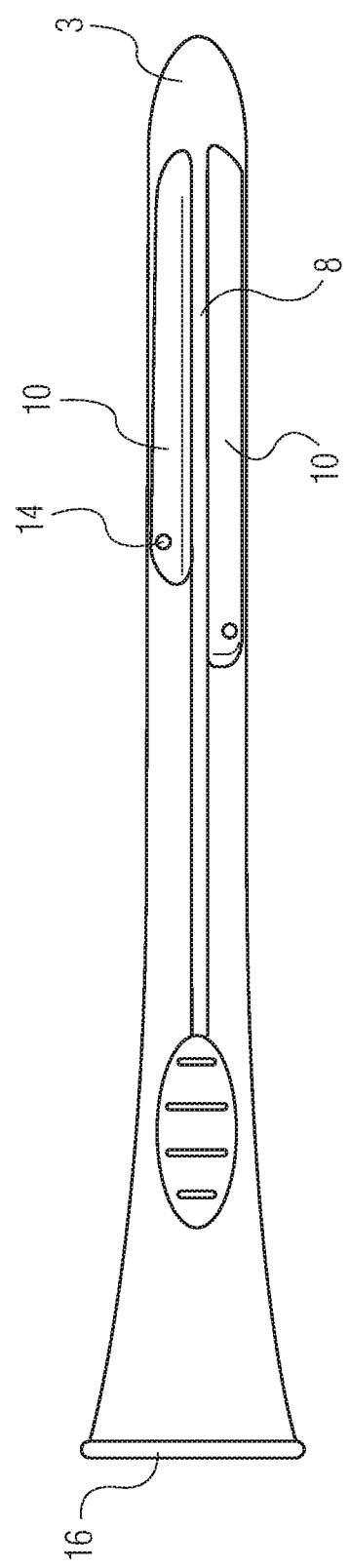
FIG. 7 shows a side view of another CIC according to the invention.

Exemplary embodiments of the present disclosure will be described hereinafter in detail with reference to the attached drawings, wherein the like reference numerals refer to the like elements. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

As shown, various embodiments of the CIC, according to the invention, allow urine to flow naturally through a urethra by using a specially designed, plastic (or other medically acceptable material) rod designed to open the urinary sphincter. In general, embodiments of the invention are directed to CICs that have a plurality of external flow paths that allow the urine to flow from the bladder, through the urethra along the external flow paths as it would under normal voiding conditions. This flow between the interior wall of the urethra and the CIC along the external flow paths, flushes any existing bacteria away from the bladder reducing the chance of a UTI.

As depicted in FIGS. 1A-1D, 7 and 8, a CIC 2 according to the invention is a one piece molded device that includes a closed solid tip 3, a distal portion 4 and a proximal portion 6. The distal portion 4 includes a plurality of elongated ribs 8 with a plurality of external flow paths 10 formed between the ribs 8. The proximal portion 6 of the CIC 2 is a tubular structure with an internal lumen 12. At the junction between the distal portion 4 and the proximal portion 6 are a plurality of lower drainage eyes 14. The lower drainage eyes 14 allow each external flow path 10 to communicate with the internal lumen 12 of the proximal portion 6. That is, each external flow path 10 terminates in a lower drainage eye 14. As can be seen in cross-section 1D-1D in FIG. 1C, the plurality of ribs 8 are in the shape of a "+" sign, however, those skilled in the art would understand that the plurality of ribs 8 could form any cross-sectional shape as long as at least one external flow path results. As can also be seen in FIGS. 1A-1D, 7 and 8, the CIC 2 includes a flared or conical proximal end 16 through which urine drains from the CIC 2. The shape of the proximal end 16 is such that it can be easily connected to a urine bag or it can be used to drain urine into another receptacle such as a toilet bowl.

In order to use the CIC 2 shown in FIGS. 1A-1D, 7 and 8, a female user grasps the CIC 2 near the proximal end 16 and inserts the solid tip 3 into the urethra. The tip 3 is advanced toward the bladder, through the urinary sphincter and into the bladder. Once the tip 3 is positioned in the bladder, urine from the bladder will drain from the bladder along the external flow paths 10, into the lower drainage eyes 14, through the internal lumen 12 and will exit the CIC 2 at the proximal end 16. As the urine flows along the external flow paths 10 between the CIC 2 and the internal wall of the urethra, any bacteria on the urethral wall will be carried away and out of the body by the flowing urine. Moreover, because the external flow paths extend almost to the tip 3 of the CIC 2, with the tip 3 positioned in the bladder, any urine contained in the bladder, including any urine at the base of the bladder, can flow out of the bladder along the external flow paths. Therefore, as long as a portion of the external flow paths 10 extends into the base of the bladder, complete voiding of the bladder can be achieved.

As shown FIGS. 2A through 3D, another CIC 20 according to the will described. The CIC 20 is a one piece molded device that includes a tip 23, a distal portion 24 and a proximal portion 26. The distal portion 24 includes a plurality of elongated ribs 28 with a plurality of external flow paths 30 formed between the ribs 28 similar to the CIC 2 of FIGS. 1A-1D. The proximal portion 26 of the CIC 20 is a tubular structure with an internal lumen 32. At the junction between the distal portion 24 and the proximal portion 26 are a plurality of lower drainage eyes 34. The lower drainage eyes 34 allow each external flow path 30 to communicate with the internal lumen 32 of the proximal portion 26. That is, each external flow path 30 terminates in a lower drainage eye 34. Similar to the CIC 2 of FIGS. 1A-1D, the plurality of ribs 28 are in the shape of a "+" sign, however, those skilled in the art would understand that the plurality of ribs could form any cross-sectional shape as long as at least one external flow path results. The CIC 20 includes a flared or conical proximal end 36 through which urine drains from the CIC 20. The shape of the proximal end 36 is such that it can be easily connected to a urine bag or it can be used to drain urine into another receptacle such as a toilet bowl. Unlike the CIC 20 of FIGS. 1A-1D, the CIC 20 of FIGS. 2A through 3D does not have a solid tip and instead has a tip 23 with an opening 38 in its distal end. The opening 38 is in fluid communication with a plurality of tip channels or lumens 40 by way of a plurality of upper drainage eyes 42. The tip lumens or channels 40 drain into or communicate with the external flow paths 30 at their proximal end 44.

In order to use the embodiment of the CIC 20, shown in FIGS. 2A through 3D, a female user grasps the CIC 20 near the proximal end 36 and inserts the tip 23 into the urethra. The tip 23 is advanced toward the bladder, through the urinary sphincter and into the bladder. Once the tip 23 is positioned in the bladder, urine from the bladder will drain from the bladder into the opening 38 in the tip 23, into the upper drainage eyes 42, through the tip lumens or channels 40, into and along the external flow paths 30, into the lower drainage eyes 34, through the internal lumen 32 and will exit the CIC 20 at the proximal end 36. As the urine flows along the external flow paths 30 between the CIC 20 and the internal wall of the urethra, any bacteria on the urethra wall will be carried away and out of the body by the flowing urine. However, in this embodiment, the external flow paths 30 may or may not enter into the bladder. If they do not enter into the bladder, urine will only drain from the bladder through the opening 38 in the tip 23. If the external flow paths 30 do enter into the bladder, urine will drain from the bladder (i) through the opening 38 in the distal tip 23 and (ii) along the external flow paths 30.

Now with reference to FIGS. 4A through 6E, another embodiment of a CIC 50 will be discussed. The CIC 50 is a one piece molded device that includes a tip 53, a distal portion 54 and a proximal portion 56. The distal portion 54 includes a plurality of elongated ribs 58 with a plurality of external flow paths 60 formed between the ribs 58 similar to the CIC 2 of FIGS. 1A-1D. The proximal portion 56 of the CIC 50 is a tubular structure with an internal lumen 62. At the junction between the distal portion 54 and the proximal portion 56 is a plurality of lower drainage eyes 64. The lower drainage eyes 64 allow each external flow path 60 to communicate with the internal lumen 62 of the proximal portion 56. That is, each external flow path 60 terminates in a lower drainage eye 64. Similar to the CIC 2 of FIGS. 1A-1E, the plurality of ribs 58 are in the shape of a "+" sign, however, those skilled in the art would understand that the plurality of ribs could form any cross-sectional shape as long as at least one external flow path results. The CIC 50 includes a flared or conical proximal end 66 through which urine drains from the CIC. The shape of the proximal end 66 is such that it can be easily connected to a urine bag or it can be used to drain urine into another receptacle such as a toilet bowl. Unlike the CIC 2 of FIGS. 1A-1E, the CIC 50 of FIGS. 4A through 6E does not have a solid tip and instead has a tip 53 that includes a plurality of elongated upper drainage eyes 68. The elongated drainage eyes 68 are in fluid communication with a plurality of tip channels or lumens 70. The tip lumens or channels 70 drain into or communicate with the external flow paths 60 at their proximal end 72.

In order to use the embodiment of the CIC 50 of FIGS. 4A through 6E, a female user grasps the CIC 50 near the proximal end 66 and inserts the tip 53 into the urethra. The tip 53 is advanced toward the bladder, through the urinary sphincter and into the bladder. Once the tip 53 is positioned in the bladder, urine from the bladder will drain from the bladder into the plurality of elongated upper drainage eyes 68, into and through the tip lumens or channels 70, into and along the external flow paths 60, into the lower drainage eyes 64, through the internal lumen 62 and will exit the CIC 50 at the proximal end 66. As the urine flows along the external flow paths 60 between the CIC 50 and the internal wall of the urethra, any bacteria on the urethra wall will be carried away and out of the body by the flowing urine. However, in the shown embodiment, the external flow paths 50 may or may not enter into the bladder. If they do not enter into the bladder, urine will only drain from the bladder through the plurality of elongated upper drainage eyes 68 in the tip 53. If the external flow paths 60 do enter into the bladder, urine will drain from the bladder (i) through the plurality of elongated upper drainage eyes 68, and (ii) along the external flow paths 60.

It is possible in other embodiments, based on the type of material that is used to mold the CIC, the CIC may buckle during urethral insertion at the junction between the distal portion and proximal portion because the lower drainage eyes are positioned at the same location along the length of the CIC. Buckling may result because of less material being in this area of the CIC making the CIC less rigid and more flexible in this region. As can best be seen in FIG. 7 (see also FIGS. 3A-3D and 5A-5D), one way to address this potential problem is to vary the length of the ribs 8, 28, 58 and hence the length of the external flow paths 10, 30, 60, thereby staggering the location of the lower drainage eyes 14, 34, 64. Staggering the location of the lower drainage eyes 14, 34, 64 along the length of the CIC increases the rigidity of the device at the junction between the distal portion and proximal portion, which helps prevent buckling of the CIC as it is inserted into the urethra.

Figure 8:
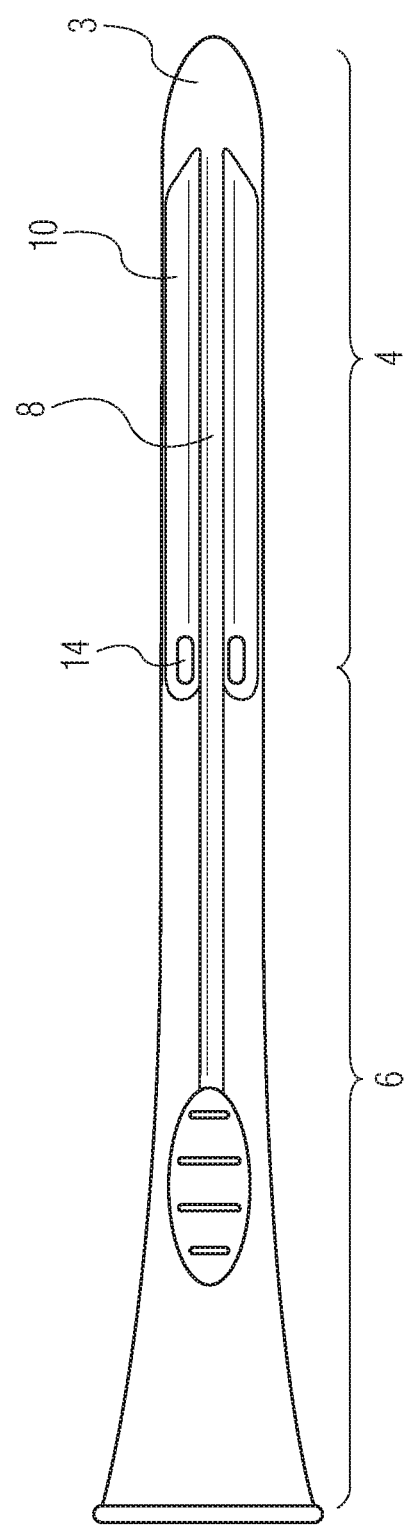
FIG. 8 shows a side view of another CIC according to the invention.
Figure 9A:
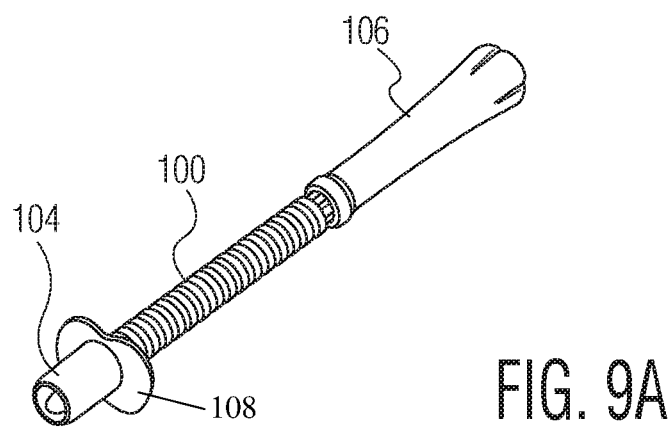
FIG. 9A shows a front perspective view of another CIC according to the invention having a flexible outer sleeve.
Figure 9B:
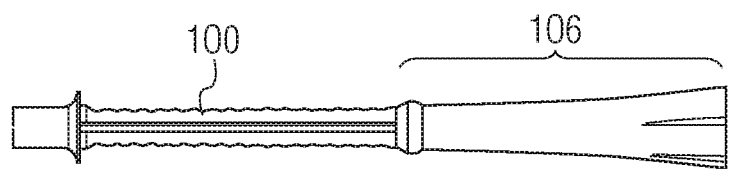
FIG. 9B shows a side view of the CIC of FIG. 9A, with the flexible outer sleeve extended.
Figure 9C:
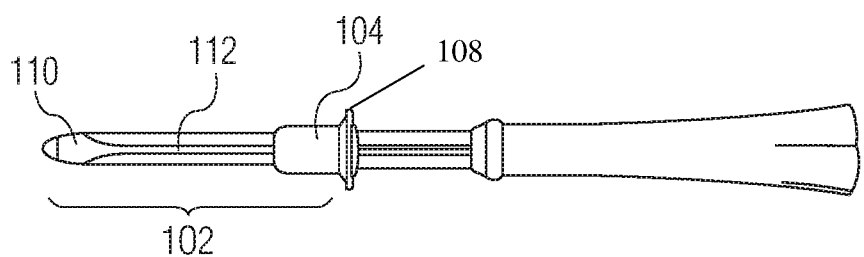
FIG. 9C shows another side view of the CIC of FIG. 9B, with the flexible outer sleeve compressed.
Figure 9D:
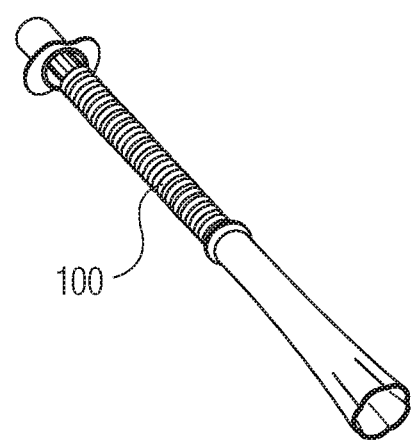
FIG. 9D shows a rear perspective view of the CIC of FIG. 9A with the flexible outer sleeve fully extended.
Figure 9E:
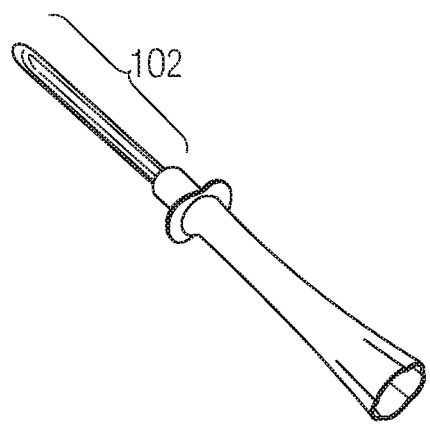
FIG. 9E shows a rear perspective view of the CIC of FIG. 9A with the flexible outer sleeve fully compressed.
Figure 9F:
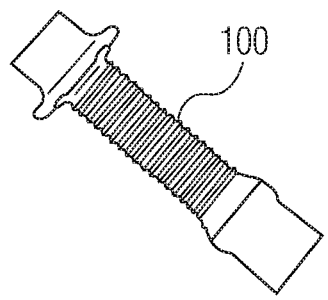
FIG. 9F shows a perspective view of the flexible outer sleeve fully.
Figure 9G:
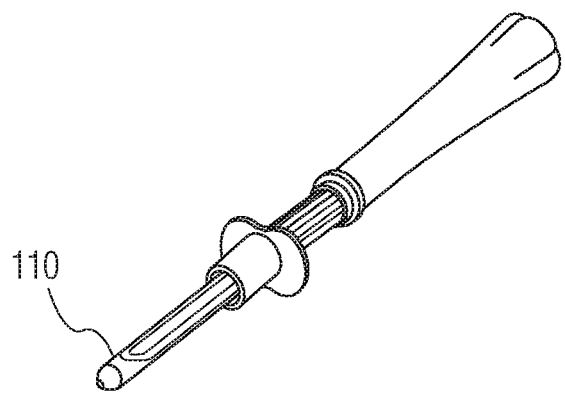
FIG. 9G shows a front perspective view of the CIC of FIG. 9A with the flexible outer sleeve partially compressed.
Figure 9H:
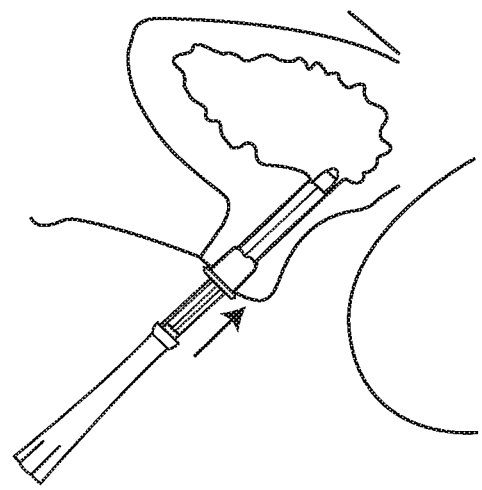
FIG. 9H shows a schematic diagram of the CIC of FIG. 9A being inserted into the human urethra.
Figure 9I:
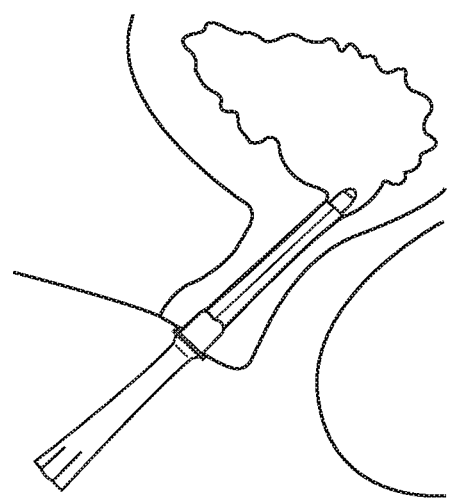
FIG. 9I shows another schematic diagram of the CIC of FIG. 9A after being inserted into the human urethra.
Figure 10A:
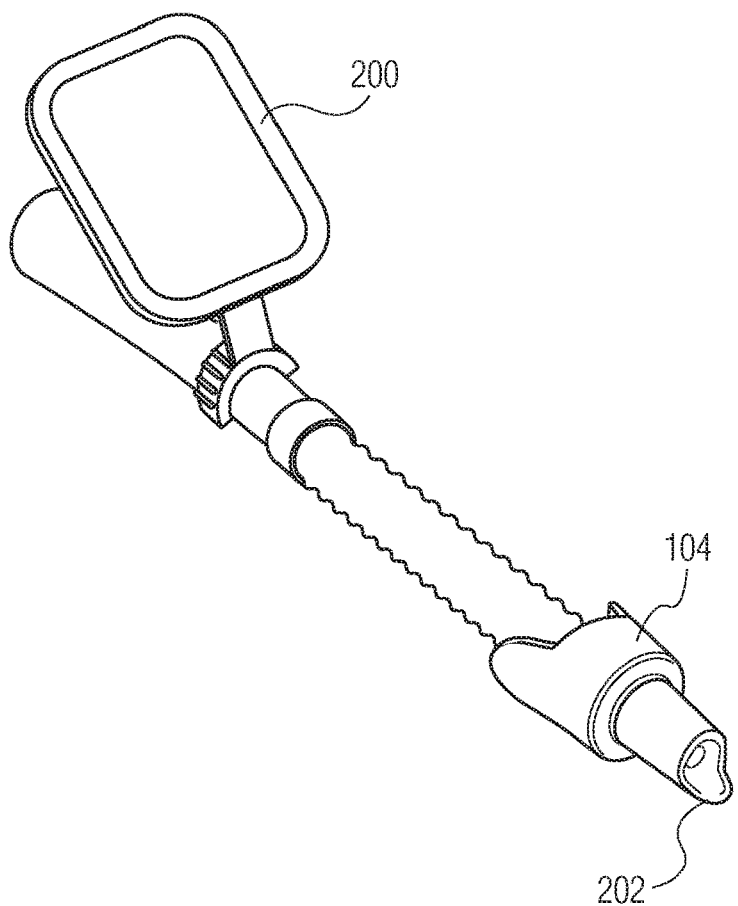
FIG. 10A shows a front perspective view of another CIC according to the invention having a mirror.
Figure 10B:
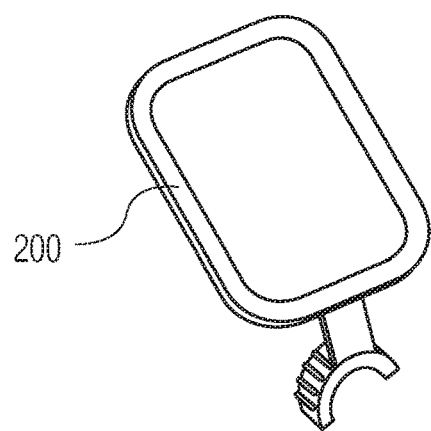
FIG. 10B shows a perspective view of the mirror of FIG. 10A.
Figure 10C:
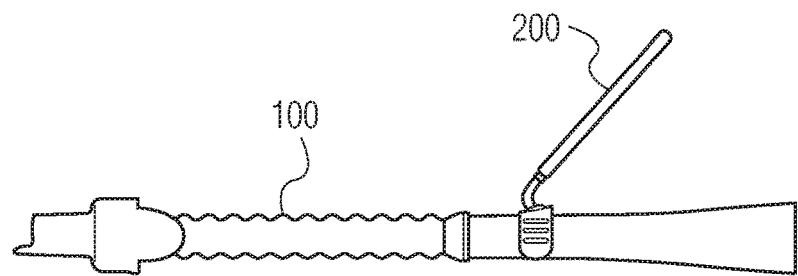
FIG. 10C shows a side view of the CIC of FIG. 10A.
Figure 10D:
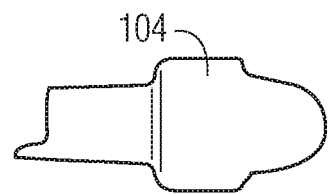
FIG. 10D shows a close up, side view of a tip member of the CIC of FIG. 10A.
Figure 10E:
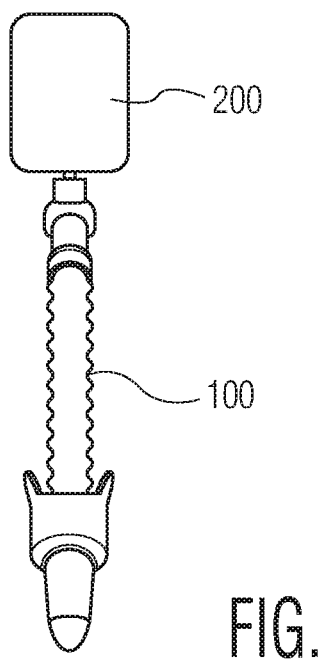
FIG. 10E shows a top view of the CIC of FIG. 10A.
Figure 11A:
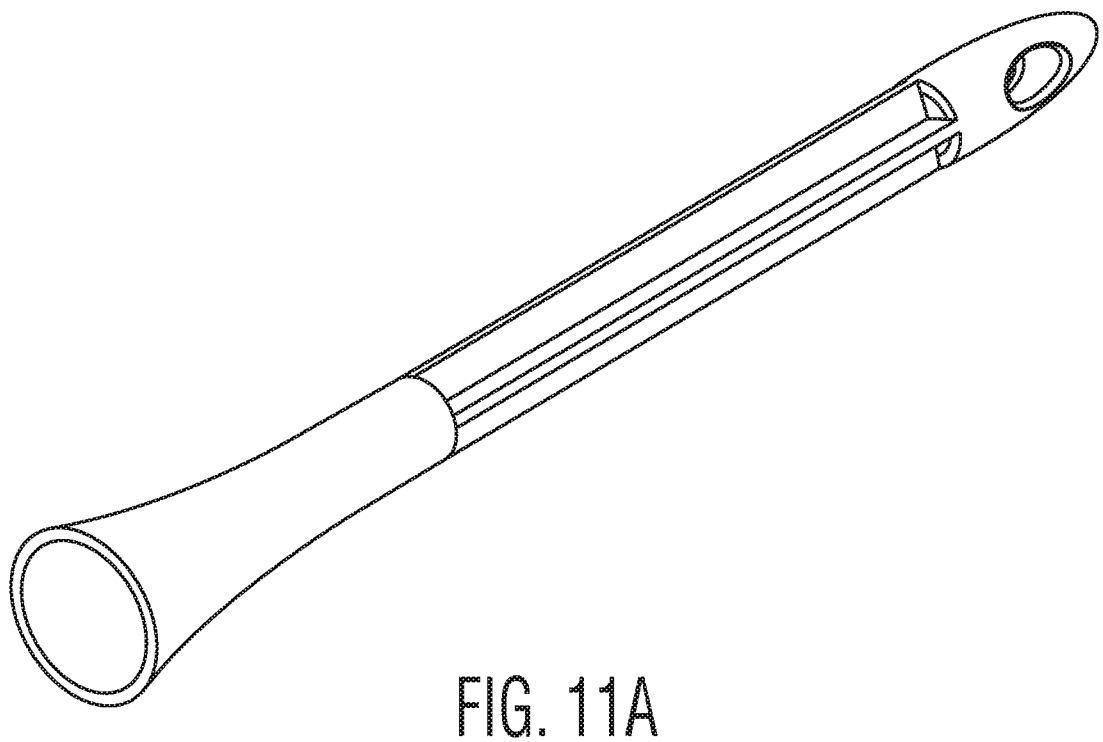
FIG. 11A shows a perspective view of another CIC according to the invention.
Figure 11B:
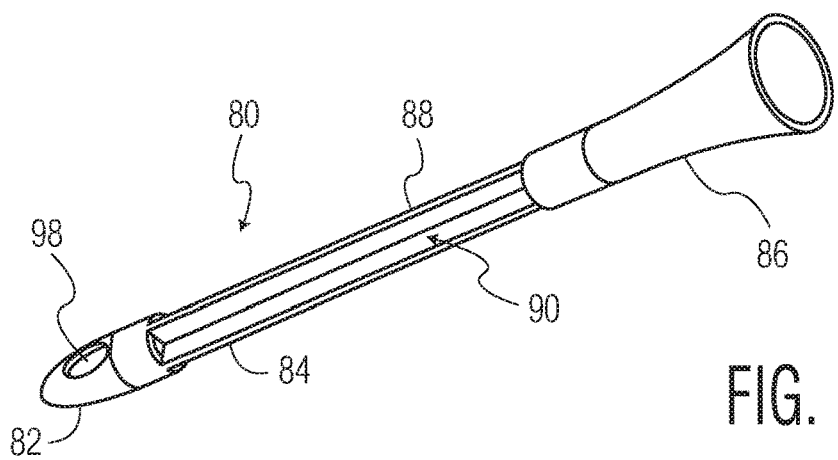
FIG. 11B shows another perspective view of the CIC of FIG. 11A.
Figure 11C:
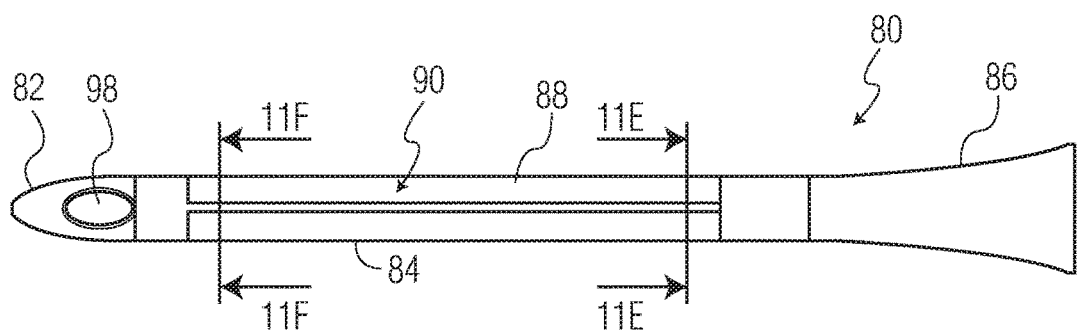
FIG. 11C shows a side view of the CIC of FIG. 11A.
Figure 11D:
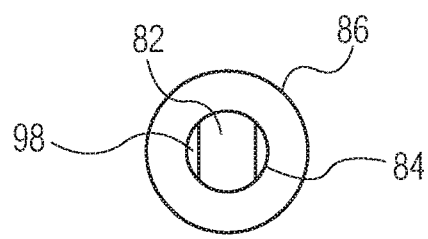
FIG. 11D shows a rear view of the CIC of FIG. 11A.
Figure 11E:
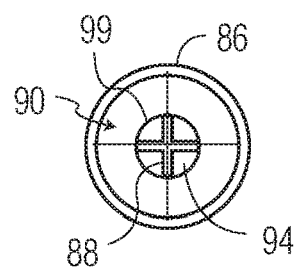
FIG. 11E shows a front view of the CIC of FIG. 11A.
Figure 11F:
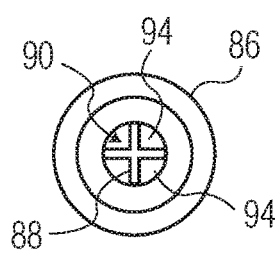
FIG. 11F is a sectional view of the CIC of FIG. 11A, taken along line 11F-11F.

As can best be seen in FIG. 8 (see also FIG. 6A-6E), another way to increase the rigidity of the device at the junction of the distal portion and proximal portion is to have the ribs 8, 58 increase in thickness along their length towards the distal portion.

Now with reference to FIGS. 9A-9I, another embodiment of a CIC according to the invention is shown, which has many features of the embodiments of the CIC disclosed above. However, the CIC of FIGS. 9A-9I includes a flexible outer sleeve 100, which may be in the form of a bellows. The flexible sleeve 100 surrounds the distal portion 102 of the CIC and includes a tip member 104. The flexible sleeve 100 attaches to the proximal portion 106 of the CIC at the junction between the distal portion 102 and proximal portion 106. In use, as depicted in FIGS. 9A-9I, the tip member 104 is inserted into the urethra. Flange portions 108 on the tip member 104 hold the tip member 104 in place at the base of the urethra. As a user continues to insert the CIC into the urethra, with the flange portions 108 holding the tip member 104 in place, the tip 110 of the distal portion 102 exits the flexible sleeve 100 and enters the urethra. As the tip 110 continues to be inserted toward the bladder, the flexible sleeve 100 compresses. Once the tip 110 enters the bladder, urine drains from the bladder along the external flow paths 112, into the proximal portion 106 and the out of the CIC. When draining is completed, the user can remove the CIC from the urethra. As the CIC is removed from the urethra, the flexible sleeve 100 expands, covering up the external flow paths 112 that are now wet with urine, thereby protecting the users fingers from touching urine.

With reference to FIG. 10A-10E, any of the above described CIC's may include a mirror 200 that can aid a user when inserting the tip of the CIC into the urethra. In addition, the tip member 104 of FIG. 10A-10E may include a protrusion 202 that can also aid a user in locating the urethra for insertion of the CIC.

Now with reference to FIGS. 11A-11D, another embodiment of a CIC 80 will be discussed. Like the CIC 50, shown in FIG. 4A-6E, the CIC 80 is a molded device that includes a tip 82, a distal portion 84 and a proximal portion 86. The distal portion 84 includes a plurality of elongated ribs 88 with a plurality of external flow paths 90 formed between the ribs 88, also similar to the CIC 2 of FIGS. 1A-1D. The proximal portion 86 of the CIC 80 is a tubular structure with an internal lumen 92. At the junction between the distal portion 84 and the proximal portion 86 is a plurality of lower drainage eyes 94. The lower drainage eyes 94 allow each external flow path 90 to communicate with the internal lumen 92 of the proximal portion 86. That is, each external flow path 90 terminates in a lower drainage eye 94. Similar to the CIC 2 of FIGS. 1A-1E, the plurality of elongated ribs 88 are in the shape of a "+" sign, however, those skilled in the art would understand that the plurality of ribs could form any cross-sectional shape as long as at least one external flow path results. The CIC 80 also includes a flared or conical proximal end 95 through which urine drains from the CIC 80. The shape of the proximal end 86 is such that it can be easily connected to a urine bag or it can be used to drain urine into another receptacle such as a toilet bowl. Like the CIC 50 of FIGS. 4A through 6E, the CIC 80 includes a tip 82 having a plurality of elongated upper drainage eyes 98. The elongated drainage eyes 98 are in fluid communication with an internal lumen, a plurality of tip channels or lumens 99. The internal lumen, tip lumens or channels 99 drain into or communicate with the external flow paths 90 at their proximal end.

In order to use the embodiment of the CIC 80, a user grasps the CIC 80 near the proximal end 86 and inserts the tip 82 into the urethra. The tip 82 is advanced toward the bladder, through the urinary sphincter and into the bladder. Once the tip 82 is positioned in the bladder, urine from the bladder will drain from the bladder into the plurality of elongated upper drainage eyes 98, into and through the internal lumen, tip lumens or channels 99, into and along the external flow paths 90, into the lower drainage eyes 94, through the internal lumen 92 and will exit the CIC 80 at the proximal end 86. As the urine flows along the external flow paths 90 between the CIC 80 and the internal wall of the urethra, any bacteria on the urethra wall will be carried away and out of the body by the flowing urine. However, in the shown embodiment, the external flow paths 90 are positioned in the urethra before entrance to the bladder. If they do not enter into the bladder, urine will only drain from the bladder through the plurality of elongated upper drainage eyes 98 in the tip 82. If the external flow paths 90 do enter into the bladder, urine will drain from the bladder (i) through the plurality of elongated upper drainage eyes 98, and (ii) along the external flow paths 90.

It is possible in other embodiments, based on the type of material that is used to mold the CIC, the CIC may buckle during urethral insertion at the junction between the distal portion and proximal portion because the lower drainage eyes are positioned at the same location along the length of the CIC. Buckling may result because of less material being in this area of the CIC making the CIC less rigid and more flexible in this region.

In all of the embodiments disclosed herein, there need not be a plurality of ribs that form a plurality of external flow paths. It is sufficient to have a configuration of the distal portion that includes at least one external flow path. Those skilled in the art would understand that the number of lower drainage eyes corresponds to the number of external flow paths.

It is to be understood that this invention is not limited to the specific devices, methods, conditions, or parameters described and/or shown herein, and that the terminology used herein is for the purpose of describing particular embodiments by way of example only. Thus, the terminology is intended to be broadly construed and is not intended to be limiting of the disclosed invention. For example, as used in the specification including the appended numbered paragraphs, the singular forms "a," "an," and "one" include the plural, the term "or" means "and/or," and reference to a particular numerical value includes at least that particular value, unless the context clearly dictates otherwise. In addition, any methods described herein are not intended to be limited to the sequence of steps described but can be carried out in other sequences, unless expressly stated otherwise herein. And any dimensions shown in the attached drawings are representative and not limiting of the invention, as larger or smaller dimensions can be used as desired.

Although the present invention has been described above in terms of exemplary embodiments, it is not limited thereto. Rather, the appended numbered paragraphs should be construed broadly to include other variants and embodiments of the invention which may be made by those skilled in the art without departing from the scope and range of equivalents of the invention.

What is claimed is:

1. A catheter comprising:
    a distal portion having a tip, a plurality of elongated ribs extending parallel to an axis of the catheter, and a plurality of external flow paths;
    a proximal portion having an internal lumen and a proximal end; and
    a plurality of drainage eyes disposed at a junction between the distal portion and the proximal portion and communicating with the plurality of external flow paths and the internal lumen.

2. The catheter according to claim 1, wherein the tip is a closed tip.

3. The catheter according to claim 2, wherein the plurality of external flow paths extend into the plurality of drainage eyes.

4. The catheter according to claim 3, wherein the plurality of drainage eyes extend into the internal lumen that extends to the proximal end.

5. The catheter according to claim 1, further comprising a solid body portion positioned between the distal portion and the proximal portion.

6. The catheter according to claim 5, wherein the solid body portion includes a plurality of elongated ribs extending therefrom and forming a plurality of external flow paths.

7. The catheter according to claim 5, wherein the plurality of elongated ribs separating the plurality of external flow paths are curved along a longitudinal axis of the solid body portion.

8. The catheter according to claim 7, wherein an outer diameter of the catheter tapers from the distal portion to the proximal portion.

9. A catheter comprising:
    a distal portion having a tip, a plurality of elongated ribs, and a plurality of external flow paths;
    a proximal portion having an internal lumen and a proximal end;
    a plurality of drainage eyes disposed at a junction between the distal portion and the proximal portion and communicating with the plurality of external flow paths and the internal lumen; and
    wherein the plurality of elongated ribs are separating the plurality of external flow paths and are curved along a longitudinal axis of a solid body portion.

10. The catheter according to claim 9, wherein the tip is a closed tip.

11. The catheter according to claim 9, wherein the plurality of external flow paths extend into the plurality of drainage eyes.

12. The catheter according to claim 11, wherein the plurality of drainage eyes extend into the internal lumen that extends to the proximal end.

13. The catheter according to claim 9, wherein the solid body portion is positioned between the distal portion and the proximal portion.

14. The catheter according to claim 13, wherein said plurality of elongated ribs are extending from said solid body portion.

15. The catheter according to claim 9, wherein an outer diameter of the catheter tapers from the distal portion to the proximal portion.

* * * * *